United States Patent [19] … [11] Patent Number: 5,380,429
Ito et al. … [45] Date of Patent: Jan. 10, 1995

[54] VARIABLE-POSITION CROSS-AXIS SYNCHRONOUS COIL PLANET CENTRIFUGE FOR COUNTERCURRENT CHROMATOGRAPHY

[75] Inventors: Yoichiro Ito, Bethesda, Md.; Kazufusa Shinomiya, Chiba, Japan

[73] Assignee: The United States of America as represented by the Deparment of Health and Human Services, Washington, D.C.

[21] Appl. No.: 27,111

[22] Filed: Mar. 4, 1993

[51] Int. Cl.$^6$ ............................................. B01D 15/08
[52] U.S. Cl. .................................. 210/198.2; 210/635; 210/657
[58] Field of Search ................ 96/101, 106; 210/198.2, 210/232, 512.1, 657, 787, 635

[56] References Cited

U.S. PATENT DOCUMENTS 5,024,758  6/1991  Ito ........................................ 210/657
5,104,531  4/1992  Ito et al. ............................ 210/198.2
5,114,589  5/1992  Shibusawa ......................... 210/198.2

OTHER PUBLICATIONS

Yoichiro Ito, "Cross-Axis Synchronous Flow-Through Coil Planet Centrifuge Free of Rotary Seals for Preparative Countercurrent Chromatography. Part 1. Apparatus and Analysis of Acceleration", in: Separation Science and Technology 22 (8-10), 1972, pp. 1971-1987.

Y. Ito, "High-speed countercurrent chromatography", reprinted from: Nature, vol, 326, No. 6111, Mar. 26, 1987, pp. 419-420.

Yoichiro Ito, "Cross-Axis Synchronous Flow-Through Coil Planet Centrifuge Free of Rotary Seals for Preparative Countercurrent Chromatography. Part II. Studies on Phase Distribution and Partition Efficiency in Coaxial Coils", in: Separation Science and Technology 22(8-10), 1987, pp. 1989-2009.

Yoichiro Ito and Tian-You Zhang, "Cross-Axis Synchronous Flow-Through Coil Planet Centrifuge For Large-Scale Preparative Counter-Current Chromatography", in: Journal of Chromatography, 449 (1988), pp. 135-151.

Yoichiro Ito and Tian-You Zhang, "Cross-Axis Synchronous Flow-Through Coil Planet Centrifuge For Large-Scale Preparative Counter-Current Chromatography, II. Studies On Partition Efficiency in Short Coils and Preparative Separations with Multilayer Coils" in: Journal of Chromatography, 449 (1988), pp. 153-164.

Yoichiro Ito and Tian-You Zhang, "Cross-Axis Synchronous Flow-Through Coil Planet Centrifuge For Large-Scale Preparative Counter-Current Chromatography. III. Performance of Large-Bore Coils in Slow Planetary Motion", in: Journal of Chromatography, 449 (1988), pp. 152-1624.

Walter D. Conway, *Countercurrent Chromatography*, VCH Publishers, Inc., New York 1990.

Hans J. Cahnmann, et al, "Synthesis and Characterization of N-bromoacetyl-3,3',5-triiodo-L-hyronine", in: Journal of Chromatography, 538 (1991), pp. 165-175.

Yoichiro Ito, et al, "Improved high-speed counter-current chromatograph with three multilayer coils connected in series" IV. Evaluation of preparative capability with large multilayer cells, in: Journal of Chromatography, 538 (1991), pp. 81-85.

(List continued on next page.)

*Primary Examiner*—Joseph W. Drodge
*Attorney, Agent, or Firm*—Townsend and Townsend Khourie and Crew

[57] ABSTRACT

A cross-axis synchronous flow-through coil planet centrifuge is disclosed which provides changeability in the position of the coils relative to the axis of rotation of the centrifuge. The advantage of such a feature is to allow adjustment of the centrifugal force operating on the coils to accommodate different types of separations. The coils are arranged in columns which are mounted to column holders that in turn can be engaged to the rotary frame of the centrifuge in positions in which the column holders intersect and do not intersect the rotary frame axis.

5 Claims, 2 Drawing Sheets

OTHER PUBLICATIONS

Yoichiro Ito, et al, "Cross-axis synchronous flow-through coil planet centrifuge (Type XLL). I. Design of the apparatus and studies on retention of stationary phase", in: Journal of Chromatography, 538 (1991) pp. 59–66.

Adrian Weisz, et al, "Complementary use of counter-current chromatography and preparative reversed-phase high-performance liquid chromatography in the separation of a synthetic mixture of brominated tetrachlorofluoresceins", in: Journal of Chromatography, 607 (1992), pp. 47–53.

Yoichiro Ito, "High-Speed Countercurrent Chromatography", in: CRC Critical Reviews in Analytical Chemistry, vol. 17, Issue 1.

VARIABLE-POSITION CROSS-AXIS SYNCHRONOUS COIL PLANET CENTRIFUGE FOR COUNTERCURRENT CHROMATOGRAPHY

This invention lies in the field of countercurrent chromatography, and relates in particular to the apparatus in which this type of chromatography is performed.

BACKGROUND OF THE INVENTION

Countercurrent chromatography (CCC) is a form of liquid-liquid partition chromatography which relies on continuous contact between two immiscible solvents, one of which is mobile relative to the other, in a flow-through tubular column, free of any solid support matrix. The retention time of a solute in the phase contact region of the system is determined by the volume ratio of the solvents, the partition coefficient of each solute between the solvents, and the degree of contact of the solvents with each other. Like other forms of liquid-liquid partition chromatography, one of the solvents serves as a carrier, drawing the solutes from the other at varying rates depending on the partition coefficients and carrying the solutes out of the column in the order of elution. This solvent can thus be referred to as the mobile phase, while the other solvent can be referred to as the stationary phase, event though it is not strictly stationary in many applications of the method. Solvent mixing in the column, retention of the stationary phase in the column, and solute partitioning in the column are all achieved with the aid of a suitable acceleration field established by gravity, centrifugal force or both, and the configuration of the column.

Most equipment used for CCC separations involves a coil of column tubing, a portion of which is filled with the stationary phase while the mobile phase is passed through it. By varying the length and diameter of the tubing, CCC has been used for both analytical and preparative separations. The flow rate of the mobile phase may be varied by varying the field imposed on the column. Units which operate with only a gravitational field imposed on the system are restricted to slow flow rates to avoid displacing the stationary phase, and the resulting separations typically require 1 to 3 days. By supplementing gravitational force with centrifugal force, one can achieve acceleration fields of 40 g or more, permitting faster flow rates which result in shorter separation times such as a few hours.

Countercurrent chromatography theory and apparatus are described in the literature. Examples of such disclosures are Ito Y., "Principle and Instrumentation of Countercurrent Chromatography," in *Countercurrent Chromatography: Theory and Practice*, Mandava, N.B. and Ito, Y., eds., pp. 79–442 (Marcel Dekker, New York, 1988); Conway, W.D., *Countercurrent Chromatography: Apparatus, Theory and Applications* (VCH, New York, 1990); and Shibusawa, Y., et al., U.S. Pat. No. 5,114,589, issued May 19, 1992.

Various types of rotation have been studied in attempts to vary the centrifugal force on the column. The optimal centrifugal force and the mode of rotation which gives rise to such a force will vary depending on the particular separation sought. One type of apparatus described in the literature for providing the centrifugal force is a cross-axis synchronous flow-through planet centrifuge, so called because of its ability to permit flow through a coiled column while rotating the column under two types of rotation at the same time—a rotation of the coiled column about its own axis, and a planetary rotation of the coiled column about an axis external to the coil. The present invention resides in an improvement in centrifuges of this type, permitting adjustment and variability of the placement of the coiled column on the centrifuge such that one can select a preferred mode of rotation for a particular separation.

SUMMARY OF THE INVENTION

A cross-axis synchronous flow-through coil planet centrifuge as it is known in the art contains two coils of tubing connected in series to serve as columns in which the phase contact is made, a rotary frame which supports the two coiled columns on opposing sides of the frame's axis of rotation, and associated tubing to permit the mobile phase to flow between the two coiled columns and to pass through the system so that eluted fractions can be collected. The present invention resides in a centrifuge in which each of the coiled columns can be placed on the centrifuge in any of two or more positions relative to the axis of rotation of the centrifuge. In each of the various positions for a given column, the axis of the column remains parallel. In preferred embodiments, the column axis in one of the positions intersects the axis of rotation of the centrifuge, while in the remaining position(s) the column axis does not intersect the axis of rotation of the centrifuge. The changing of each column from one position on the rotary frame to the next is achieved by the use of releasable mounting fixtures on the column holders, the fixtures being constructed to permit releasable securement to two or more positions on the rotary frame.

In further preferred embodiments of the invention, the flexible tubing which connects the coiled columns, supplies the mobile phase to the coiled columns, and carries the eluent to the point where fractions are collected is held in tubing guides, which are rigid cylindrical tubes mounted on the rotary frame together with the coiled columns. The tubing guides are mounted with axes parallel to those of the coiled columns, and are supplied with releasable mounting fixtures as well, so that they can be repositioned to accommodate changes in the mounting positions of the coiled columns. In still further preferred embodiments, the mounting fixtures on the tubing guides and those on the column holders are interchangeable so that either a tubing guide or a column holder can be engaged with a single engagement member on the rotary frame. Mechanisms are also provided which impart rotational motion to the tubing guides to complement that rotational motion of the coiled columns, thereby preventing the twisting of the flexible tubing.

These and other features, advantages and embodiments of the invention will become apparent from the description which follows.

DESCRIPTION OF THE PREFERRED EMBODIMENTS

Figure 1:
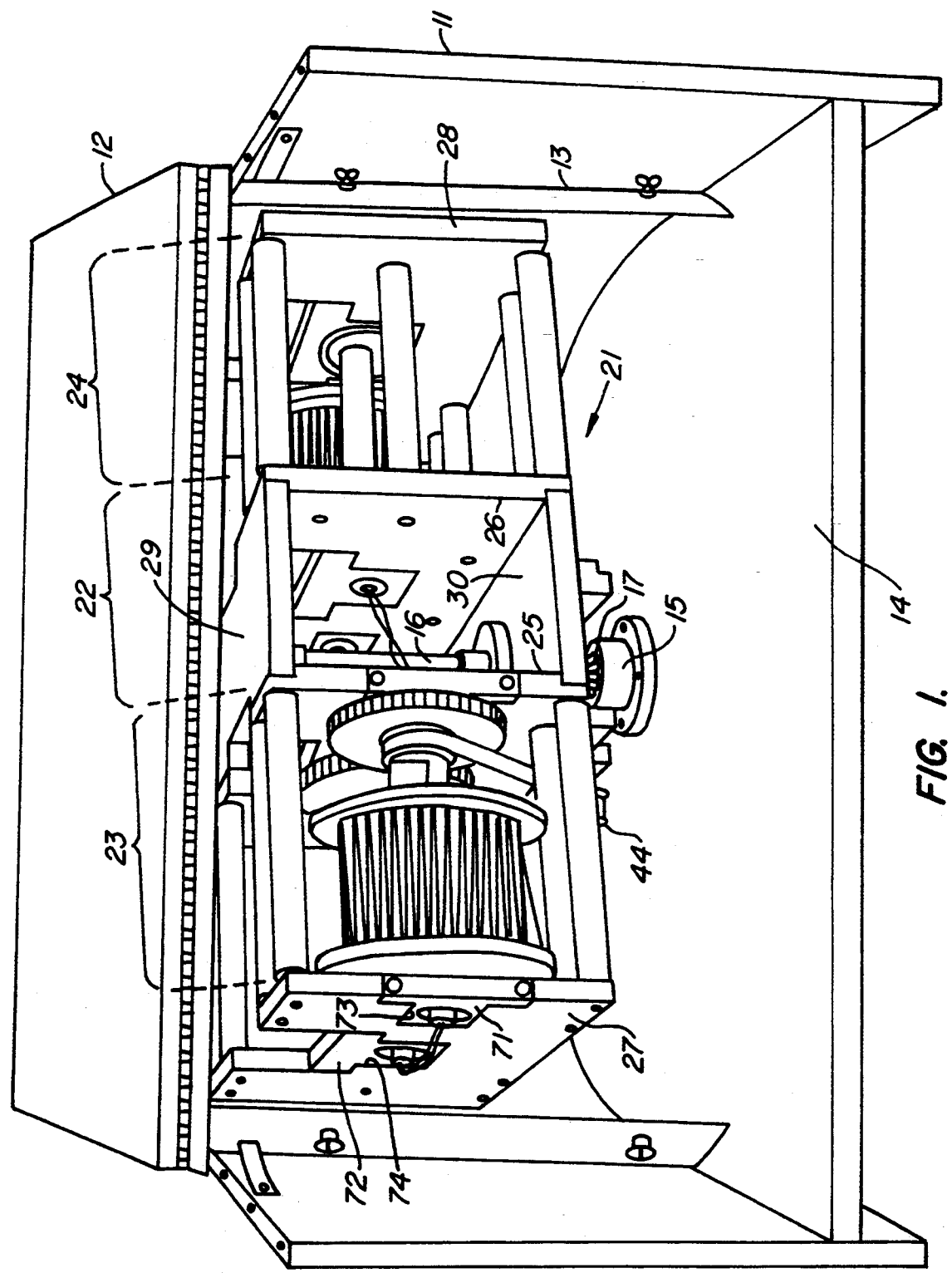
FIG. 1 is a perspective view of an illustrative cross-axis synchronous flow-through coil planet centrifuge in accordance with the present invention, with wall portions removed to show the interior.

While this invention is varied in scope and encompasses many distinct embodiments, the invention can be readily understood by a detailed review of one particular embodiment. The following description focuses on the embodiment shown in the drawings.

In the perspective view of FIG. 1, a housing 11 is shown with one wall removed (i.e., a front wall parallel to the plane of the drawing) to show the interior. The housing has a lid 12 which is shown folded back for further visibility of the interior. Contained within the housing is a cylindrical shield 13, a front section of which has been removed to allow visibility of the components inside.

Affixed to the floor 14 of the housing is a cylindrical boss 15 with an axial hole through which passes a rotary shaft 16 which forms the central axis of the apparatus. At the top of the boss and surrounding the axial hole is a tapered stationary sun gear 17, whose function will become evident from the description which follows.

Mounted to the rotary shaft 16 is a rotary frame 21, both of which rotate together. The rotary frame is divided into three compartments - a central compartment 22 which contains the rotary shaft 16, and two side compartments 23, 24. The three compartments are also visible in the horizontal cross-section view of FIG. 2. The side compartments are separated from the central compartment by inner walls 25, 26, and the side compartments terminate at their outer extremities at side walls 27, 28. The central compartment is further enclosed at the top and bottom by a top plate 29 and a bottom plate 30 (FIG. 1). The rotary shaft 16 is secured to both top and bottom plates, extending below the bottom plate down to the stationary cylindrical boss 15. The centrifuge shown in FIG. 1 is equipped with two columns, each consisting of 32 column units. The set of coil units is symmetrically arranged around the holder in parallel to and at the same distance from the holder axis. The coil units are connected in series and provide a capacity sufficient for analytical separations.

Figure 2:
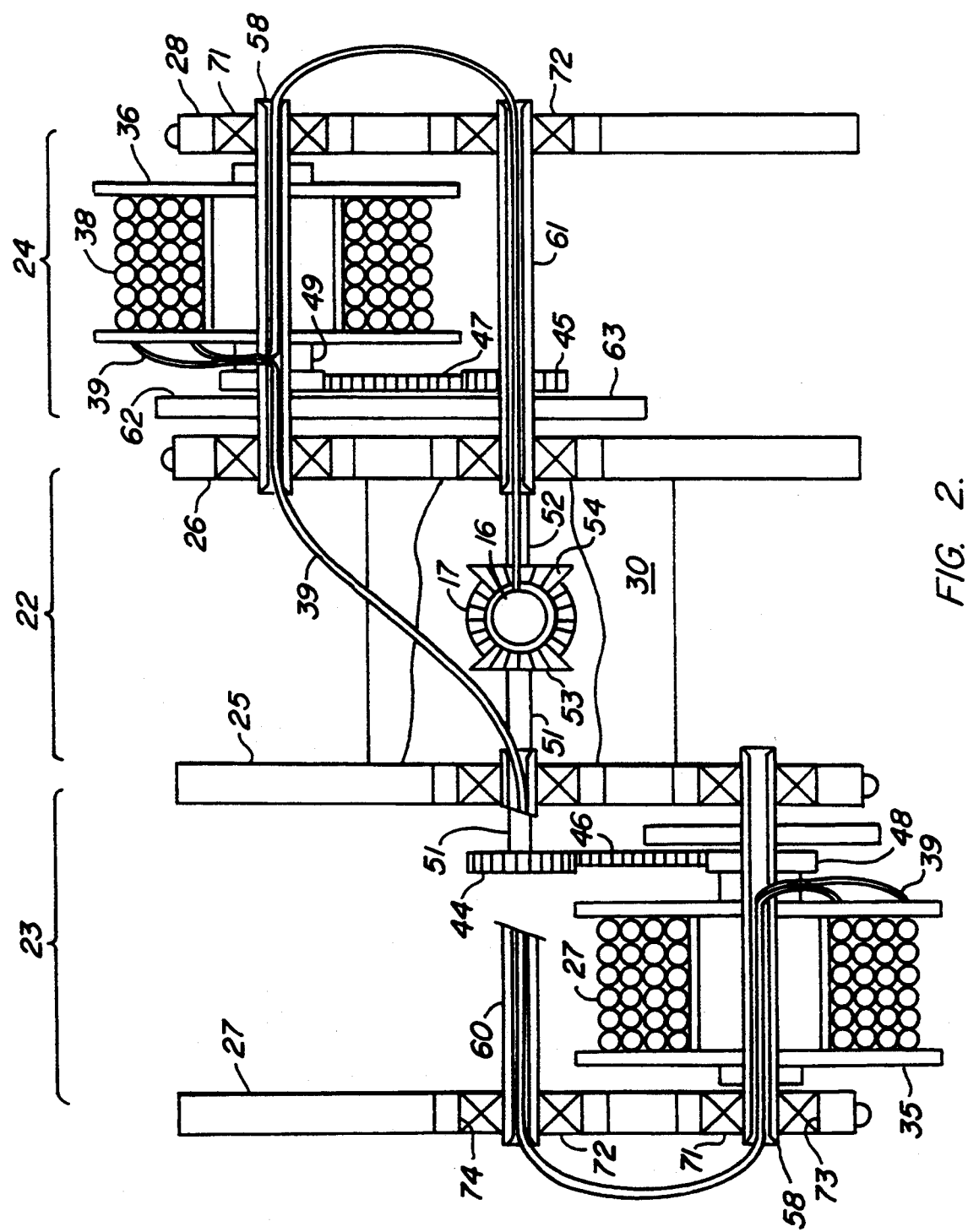
FIG. 2 is a cross section of the rotary frame portion of the centrifuge of FIG. 1, taken along a horizontal plane at mid-height.

The cross section of FIG. 2 is taken along a horizontal plane intersecting the rotary frame at mid-height. The inner walls 25, 26 and side walls 27, 28 of the rotary frame are thus shown in cross section, the top wall 29 is not shown, and the bottom wall 30 is partly broken away to show the sun gear 17 underneath on the floor of the housing.

As shown in FIG. 2, mounted inside each of the two side compartments is a column holder 35, 36. Each column holder is a spool-shaped component around which the chromatographic column 37, 38 is coiled. The coils in this embodiment are multi-layered, but form one continuous coil around each column holder. Flexible tubing 39 feeds the mobile phase to each coil at one end and carries the mobile phase away from the coil at the other end. Flexible tubing of the same type also connects the two coils to each other, and to a feed source and collection unit, neither of which are shown in the drawings. The flow through the tubing and the coils thus forms a single continuous path from the feed source, through the two coils in series, and then to the collection unit, where the eluent is divided into fractions which are individually analyzed. In this embodiment, both the tubing leading from the feed source and the tubing leading to the collection unit are located in the region of the rotary shaft 16, from which further connections of a conventional nature and construction are made to join these tubing sections to the appropriate external units.

The rotary shaft 16 is driven by a motor (not shown) beneath the bottom plate 14 of the rotary frame. Since the entire rotary frame 21 is rigidly mounted to the rotary shaft, this causes the rotary frame itself to rotate. Engaging the sun gear 17 on the floor of the housing are a pair of miter gears 53, 54, each mounted to the end of a horizontal shaft 51, 52, respectively. These horizontal shafts are rotationally mounted to the inner walls 25, 26, respectively, of the rotary frame, underneath the bottom plate 30 of the central compartment. Thus, rotation of the frame causes the horizontal shafts to travel around the sun gear, and the engagement of the sun gear with the miter gears causes the horizontal shafts to rotate around their own axes as well.

The outer ends of the horizontal shafts 51, 52 terminate in the side compartments 23, 24 in toothed pulleys 44, 45, respectively. Toothed belts 46, 47 join these toothed pulleys 44, 45 to higher toothed pulleys 48, 49 which are mounted to, and coaxial with, the column holders. The rotation of the horizontal shafts 51, 52 is thus imparted to the column holders, and the rotation of the rotary frame about its central vertical axis is this synchronized with the rotation of the column holders.

Securement of the flexible tubing connecting the two coiled columns to each other and to the feed source and collection unit is achieved by tubing guides, which are rigid sections of tubing of a diameter sufficiently large to loosely contain two such flexible tubes. One pair 58, 59 of these tubing guides passes through the axes of the column holders. A second pair 60, 61 are additional tubing sections which are mounted to the inner walls and side walls, spanning the widths of the two side compartments 23, 24, respectively. One of these additional tubing sections 60 is partially removed in the drawing to more clearly show the toothed pulley 44 and shaft 51 underneath.

It is important to avoid twisting of the flexible tubing leading to and from each coiled column as the tubing passes through the tubing guides 60, 61. Avoidance of the twisting is achieved by rotating each tubing guide at the same rate as, and in the direction opposite to that of, the rotation of the column holder in the same side compartment of the rotary frame. A toothed gear 62 is mounted to the axis of the column holder 36, the gear engaging an identical toothed gear 63 mounted to the axis of the adjacent tubing guide 61. The identical arrangement appears on the opposite column holder 35 and tubing guide 60, although the tubing guide gear on that side is not shown so that the parts underneath are visible. This synchronous motion between the tubing guide and the column holder on each side of the rotary frame eliminates any twisting or distortion of the flexible tubing.

The column holders 35, 36 and the tubing guides 60, 61 are each secured to the rotary frame 21 in such a manner that they can be removed and exchanged. In the arrangement shown in the drawings, the axes of both the column holders and the tubing guides are each horizontal and perpendicular to the central vertical axis of the rotary frame, i.e., the axis passing coaxially through the rotary shaft 16, but the axes of the column holders 35, 36 (and hence the coiled columns themselves) are offset from the central vertical axis of the rotary frame whereas the axes of the tubing guides 60, 61 intersect the central vertical axis. Exchanging each column holder with the tubing guide in the same side compartment of the rotary frame will result in the axes of the coiled columns intersecting the central vertical axis.

This exchangeability is achieved by the use of mounting members and corresponding engagement members which engage the mounting members in a releasable manner. The mounting members in this embodiment are T-shaped members 71, one secured to each end of each of the two column holders 35, 36. An identical T-shaped mounting member 72 is secured to each end of each of the two tubing guides 60, 61. The engagement members are T-shaped slots 73, 74 in the side walls 27, 28 of the rotary frame. Of the two slots in each side wall, one extends inward from each of two adjacent edges of the side wall, and one slot is deeper than the other, extending to the center of the side wall, whereas the other slot terminates short of the center. Since each slot is shaped to accommodate each mounting member, the two mounting members can be placed in either position. Thus, the arrangement of FIG. 2 can be reversed, with the column holders occupying the positions held by the tubing guides, and vice versa. Screws (not shown) secure the mounting members in place.

In a presently preferred embodiment of this invention, the apparatus measures 60 cm both in width and length and 40 cm in height. The miter gears and the sun gear are at a 45-degree angle. In both positions of the column holders, the displacement along the column holder axis between the center of the column holder and the rotary shaft of the frame is about 15 cm, and the displacement normal to the column holder axis is about 8 cm. The speed of rotation of the central vertical rotary shaft is regulated up to 1000 rpm by a speed control unit supplied by Bodine Electric Co., Chicago, Illinois, USA. The tubing guides are lubricated with grease and individually protected with a short sheath of Tygon tubing at each projecting hole to prevent direct contact with the metal parts.

The foregoing is offered primarily for purposes of illustration. It will be readily apparent to those skilled in the art that the shapes and arrangement of the parts, the mounting structures and fixtures, and the materials, operating conditions and other parameters of the centrifuge may be further modified or substituted in various ways from what is described herein without departing from the spirit and scope of the invention.

What is claimed is:

1. In a cross-axis synchronous flow-through coil planet centrifuge comprising:
   a support base,
   a rotary frame mounted to said support base for rotation about an axis defined as a rotary frame axis,
   a pair of column holders capable of being mounted to each of two opposing sides of said rotary frame for rotation relative to said rotary frame about axes defined as column holder axes, said column holder axes each being perpendicular to said rotary frame axis, and
   a coiled column mounted to each of said column holders, the improvement in which said centrifuge further comprises:
   mounting members on said column holders, and
   engagement members on said rotary frame for releasable engagement of said mounting members, with a plurality of engagement members for each said mounting member, thereby defining a plurality of mounting positions comprising one position for each said column holder in which the column holder axis thereof intersects said rotary frame axis, and at least one position for each said column holder in which the column holder axis thereof does not intersect said rotary frame axis for each said column holder on said rotary frame.

2. A cross-axis synchronous flow-through coil planet centrifuge in accordance with claim 1 further comprising:
   flexible tubing communicating said coiled columns with each other and with the exterior of said centrifuge, and
   a pair of tubing guides to support said flexible tubing, said tubing guides constructed for removable mounting to each of said two opposing sides of said rotary frame.

3. A cross-axis synchronous flow-through coil planet centrifuge in accordance with claim 2 in which said mounting members are defined as column holder mounting members, and said centrifuge further comprises tubing guide mounting members on said tubing guides, said tubing guide mounting members being adapted for engagement by said engagement members interchangeably with said column holder mounting members.

4. A cross-axis synchronous flow-through coil planet centrifuge in accordance with claim 3 in which said tubing guide mounting members permit rotation of said tubing guides relative to said tubing guide mounting members.

5. A cross-axis synchronous flow-through coil planet centrifuge in accordance with claim 4 further comprising synchronous gears mounted to said column holders and said tubing guides to cause said tubing guides and said column holders to rotate simultaneously at the same rate of rotation, thereby preventing twisting of any flexible tubing supported by said tubing guides as a result of rotation of said column holders.

* * * * *